United States Patent [19]

Woolbert et al.

[11] Patent Number: 4,852,384
[45] Date of Patent: Aug. 1, 1989

[54] AUTOMATIC CALIBRATION AND CONTROL SYSTEM FOR A COMBINED OXYGEN AND COMBUSTIBLES ANALYZER

[75] Inventors: Gordon D. Woolbert, North Canton; Scotty Y. Jewett, Lyndhurst; John W. Robertson, Jr., Chesterland, all of Ohio

[73] Assignee: The Babcock & Wilcox Company, New Orleans, La.

[21] Appl. No.: 854,256

[22] Filed: Apr. 21, 1986

[51] Int. Cl.⁴ ............................................. G01N 31/00
[52] U.S. Cl. .................................................. 73/1 G
[58] Field of Search ........................ 73/1 G; 364/571; 340/632, 633, 634

[56] References Cited

U.S. PATENT DOCUMENTS

| | | | |
|---|---|---|---|
| 3,070,988 | 1/1963 | Kapff et al. | 73/1 G |
| 3,359,784 | 12/1967 | Jorre et al. | 73/1 G |
| 3,924,442 | 12/1975 | Kerho et al. | 73/1 G |
| 4,445,359 | 5/1984 | Smith | 73/1 G |
| 4,476,706 | 10/1984 | Hadden et al. | 73/1 G |
| 4,555,930 | 12/1985 | Leach et al. | 73/1 G |
| 4,578,986 | 4/1986 | Navarre | 73/1 G |

Primary Examiner—Robert R. Raevis
Attorney, Agent, or Firm—Vytas R. Matas; Robert J. Edwards

[57] ABSTRACT

An automatic calibration and control system for a combined oxygen and combustibles analyzer comprises a process control computer which automatically calibrates a combined oxygen and combustibles analyzer. The computer initiates a calibration sequence through a mechanical unit which introduces calibration gases to the analyzer. The computer calculates a drift adjustment for both oxygen and combustibles and applies it to the incoming oxygen and combustibles signal from the analyzer to arrive at calibrated oxygen and combustibles signals. The system allows both oxygen and combustibles signals to be calibrated automatically and concurrently with minimal operator interface.

11 Claims, 4 Drawing Sheets

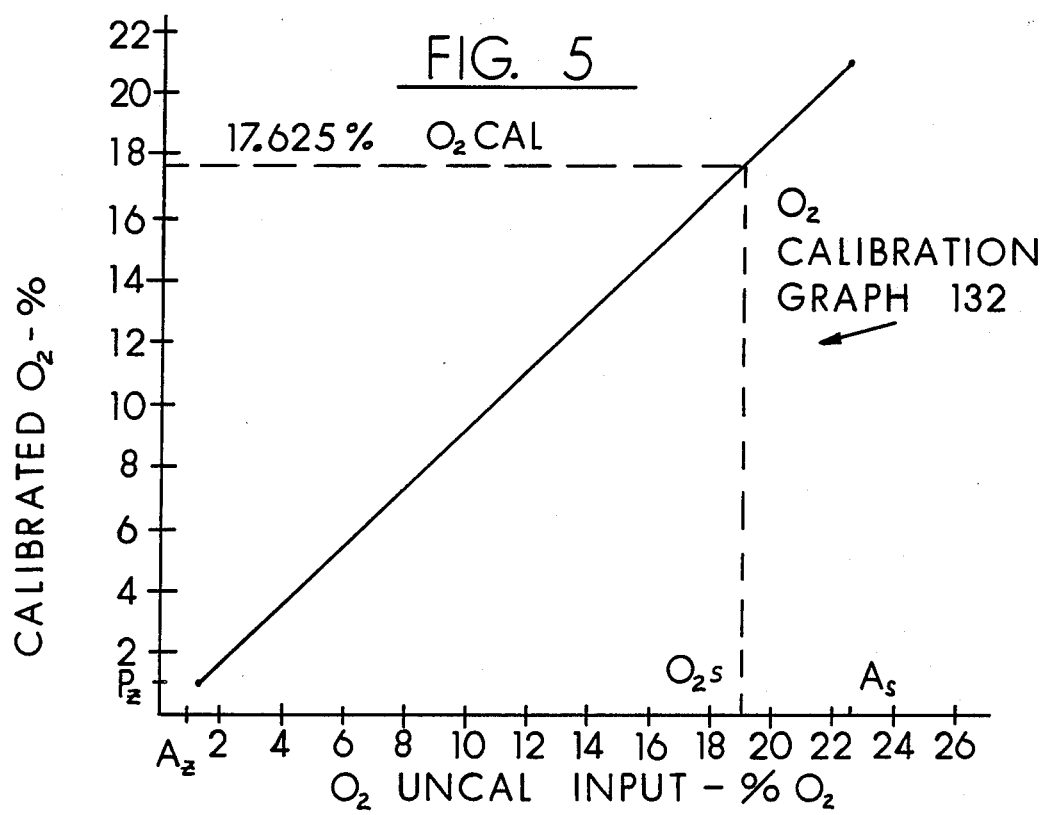
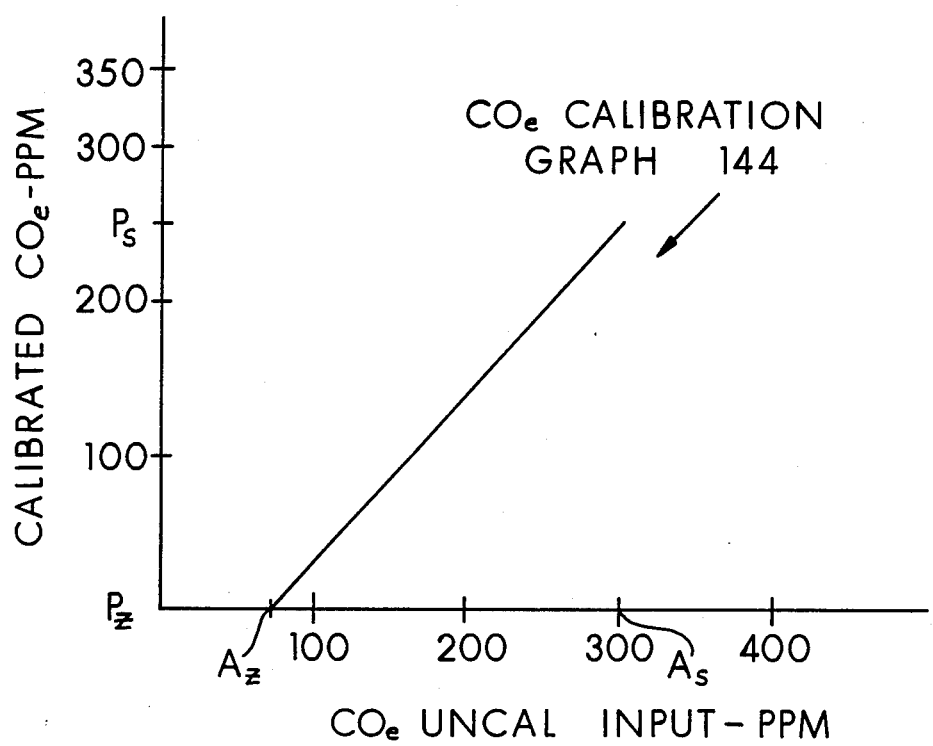

AUTOMATIC CALIBRATION AND CONTROL SYSTEM FOR A COMBINED OXYGEN AND COMBUSTIBLES ANALYZER

BACKGROUND OF THE INVENTION

1. Field of the Invention

The present invention generally relates to systems for calibration of combined oxygen and combustibles analyzers and particularly to automatic control systems for calibrating and monitoring the signals of combined oxygen and combustibles analyzers.

2. Description of Prior Art

Many known volatile atmosphere processes, such as boiler furances and coal pulverizers, require constant monitoring to detect potentially flammable or explosive conditions and alert an operator to such conditions.

Presently, several systems are being used to monitor potentially dangerous coal pulverizer atmospheres. Thermocouples and infrared gas analyzers are two systems used to monitor pulverizers. A shield is needed to protect these systems from the corrosive coal particles in the coal pulverizer. The shield reduces heat conduction to the thermocouple system thereby reducing response time. Infrared gas analyzers need to condition the sample gas also decreasing response time and sensitivity.

A more reliable method used to monitor volatile atmospheres in coal pulverizers is to provide signals indicative of either oxygen, CO, or both. A certain quantity of each of these elements in a volatile atmosphere becomes indicative as to the presence of a hazardous condition. Combination oxygen/combustibles analyzers such as the Bailey Controls Model OL230 are used to provide such signals or combinations of them.

These analyzers must be calibrated frequently to make sure that they are providing an accurate measurement of the forementioned elements in the volatile atmosphere. Presently, the calibration procedures for such analyzers are not automated with the entire analyzer control system.

The present method for calibrating these analyzers is manual. The operator manually introduces a test gas to the analyzer, maintaining the air pressure as if the analyzer was in operation. While maintaining the test gas pressure, the calibration potentiometers are manually adjusted and test voltage outputs are monitored through hand held voltmeters until the desired calibrated outputs are attained.

A known method for calibrating a combustibles signal consists of introducing a test gas to the analyzer and maintaining the sample air pressure as in the manual calibration of the oxygen signal. The zero and span (max. scale value) values from the test gas are adjusted by an operator. The incoming sample signal is then calibrated according to these adjusted values.

The known calibration systems for combination oxygen/combustibles analyzers are also manual. This inhibits the calibration of a plurality of analyzers by one operator. The oxygen calibration operation requires at least fifteen minutes of operator time. This manual operation introduces the possibility of operator error and does not allow for repeatability of zero and span values. Further, the calibration of both combustibles and oxygen signals is not coordinated and thus hinders a plurality of analyzers from being calibrated concurrently.

Since the oxygen signal can drift significantly out of calibration before an operator becomes aware of the need for recalibration, a significant error with the oxygen signal is generated by the drift before it is detected and corrected.

Thus, it is seen that an accurate and reliable automatic calibration system was required for periodically calibrating the oxygen signal of oxygen/combustibles analyzers and coordinating it into a total control system for monitor/alarm/calibration of the entire safety monitoring unit.

SUMMARY OF THE INVENTION

The present invention described herein overcomes all the prior art problems associated with non-automated control systems for oxygen/combustibles sensors as well as other problems by providing an improved safety monitoring system for oxygen and combustibles analyzers using automatic calibration. The present system coordinates an automatic periodic calibration system with a signal sensing and safety alarm system to provide an entire monitoring/alarming/calibration system for oxygen and combustibles analyzers. The system calibrates both the oxygen and combustibles signals in a fully automated fashion. A calibration procedure is initiated automatically on a predetermined interval such as every twenty-four hours. The calibration is performed concurrently on the oxygen signal and the combustible signal. Further, an alarm function is set into operation whenever the calibrated zero and span values go beyond a preset limit. Thereby the present invention insures that an accurate, hands-off calibration will be periodically performed.

Thus, one aspect of the present invention is to provide an automated system capable of periodically calibrating an oxygen and combustibles analyzer. Another aspect of the invention is to provide an automated system capable of calibrating both the oxygen and combustibles signal of an oxygen and combustibles analyzer concurrently.

Yet another aspect of the present invention is to automatically adjust both the span and zero values of both the oxygen and combustibles signals to minimize the effect of drift on the current analyzer signal.

These and other aspects of the present invention will be more fully understood upon a review of the following description of the preferred embodiment taken in conjunction with the drawings.

BRIEF DESCRIPTION OF THE DRAWINGS

FIG. 5 is an oxygen calibration graph used by the oxygen signal unit of FIG. 4.

FIG. 7 is a combustibles calibration graph used by the combustibles signal unit of FIG. 6.

DESCRIPTION OF PREFERRED EMBODIMENT

Figure 1:
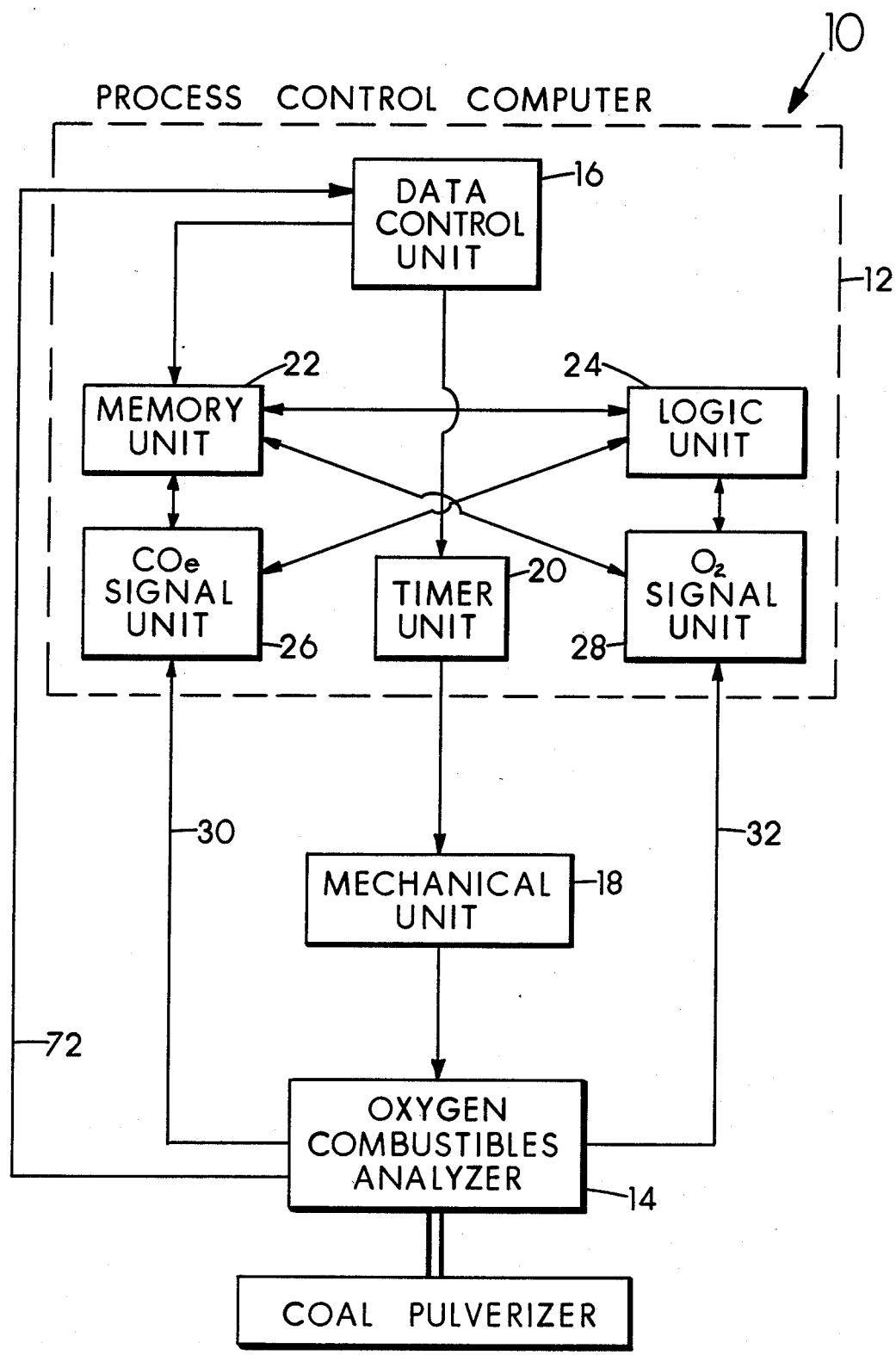
FIG. 1 is a schematic drawing of the automated calibration control system for oxygen and combustibles analyzers of the present invention.

Referring now to the drawings generally with particular reference to FIG. 1, an automatic calibration control system 10 is provided including a known process control computer 12, such as a Bailey Controls Co. Model Network 90, and a known oxygen/combustibles analyzer 14, such as a Bailey Controls Co. Model OL230 gas analyzer. All operations and calculations performed by the computer 12 use known hardware/firmware algorithms. These algorithms are called function block units because each algorithm performs a specific function. The hardware/firmware used by function blocks include combinations of microprocessors with internal, unchangeable operation commands to perform the desired function and will be referred to as units.

More particularly, the system 10 includes a data control unit 16 which energizes a mechanical unit 18, by way of a timer unit 20, allows a manual input of data to a microprocessor memory unit 22. The mechanical unit 18 allows calibration gases to be introduced to the analyzer 14. The memory unit 22 provides storage for and access to all necessary values used by the entire calibration system 10. The timer unit 20 is an internal digital clock circuit which controls all timing functions needed by the calibration system 10. As shown in FIG. 1, a logic unit 24 receives inputs from the memory unit 22 and alerts the operator if the inputs go beyond preset limits for zero and maximum scale (hereafter referred to as span) and performs calculations needed by a combustibles (hereafter referred to as $CO_e$) signal unit 26 and an oxygen (hereafter referred to as $O_2$) signal unit 28. Signal units 26 and 28 respectively perform the actual calibration on a $CO_e$ indicating signal 30 and an $O_2$ indicating signal 32, originating from the known oxygen/combustibles analyzer 14.

Figure 2:
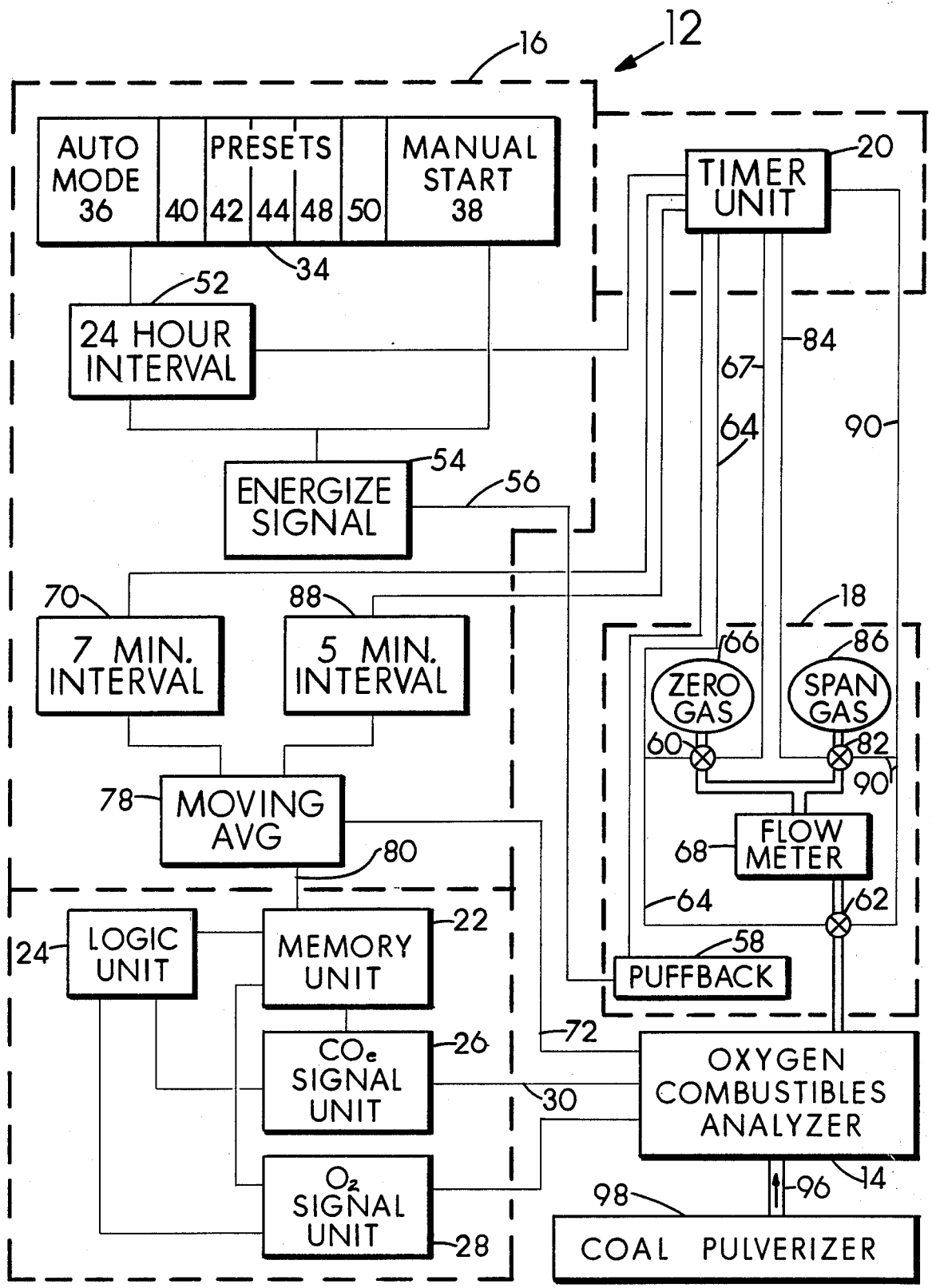
FIG. 2 is a schematic of the control logic for the data control unit and the mechanical unit of FIG. 1.

Referring now to FIG. 2, the data control unit 16 has a manual data input station 34. The manual input station 34 may be a known computerized data input keyboard or any other known manual data input apparatus. The manual data input station 34 allows an operator to selectively set the control unit 16 in an automatic mode 36, or start calibration sequence manually through a manual start button 38, preset optimum zero and span values for $CO_e$ 40,44 and $O_2$ 42,48 respectively, and preset alarm limits 50 for the forementioned optimum zero and span values. The preset values 40,42,44,48,50 may be tuned or adjusted by the operator at any time through the manual input station 34.

Usually, the control unit 16 will be set in the automatic mode 36. When in the automatic mode 36 the analyzer 14 will be calibrated on a twenty-four hour interval 52. The interval will be maintained by the timer unit 20. The timer unit 20 provides that a calibration sequence will be performed on the analyzer 14 every day to insure the accuracy of the oxygen and combustibles signals 30,32 originating from the analyzer 14. The manual start button 38 may also initiate a calibration sequence and will override the timer unit 20 to enable a calibration sequence to be performed at any time desired by the operator.

When a calibration sequence is initiated by either actuating the manual start button 38 or by the timer unit 20, an energize signal 54 is sent to the mechanical unit 18 along a line 56 from the process control computer 12. The mechanical unit 18 is physically attached by any known method to the analyzer 14.

The mechanical unit 18 begins the calibration sequence by performing a cleaning operation 58 on the analyzer 14. The cleaning operation 58 is called a puffback. In this operation the mechanical unit 18 forces air back through the analyzer 14 to clean the analyzer 14. The cleaning operation 58 is controlled by the timer unit 20 to continue for a period of ten seconds.

When the operation 58 is complete, known solenoid valves 60 and 62 are energized to open by a control signal 64 allowing a zero calibration gas 66 to flow through a flow meter 68 into the analyzer 14. The gas 66 flows through the analyzer 14 for a seven minute interval 70 as controlled by timer unit 20. The timer unit 20 sends a control signal 67 to deenergize the valve 60 when the seven minute interval 70 is over. The gas 66, used for zero calibration, usually consists of 1.0% $O_2$ and 0 ppm $CO_e$.

During the seven minute interval 70, zero value signals for $CO_e$ and for $O_2$ as sensed by the analyzer 14 are sent along a line 72 to the data control unit 16. When the seven minute interval 70 is over, a signal indicative of a one minute moving average of zero values for $CO_3$ 74 and for a signal indicative of a one minute moving average of zero values $O_2$ 76 are calculated by an internal averaging function block unit 78. These signals 74 and 76 are then sent to the memory unit 22 along a line 80.

At the end of the seven minute interval 70 a third solenoid 82 is energized by a control signal 84 originating from the timer unit 20, allowing a span gas 86 to flow through the flow meter 68 to analyzer 14. The span gas 86 usually contains 20.9% $O_2$ and 250 ppm $CO_e$. The span gas 86 flows through the analyzer 14 for a five minute interval 88. At the end of the five minute interval 88 the timer unit 20 sends a control signal 90 to deenergize valves 62 and 82.

During the five minute interval 88, span values for $CO_e$ and $O_2$ as sensed by analyzer 14 are sent to the data control unit 16 along the line 72. When the five minute interval 88 lapses a one minute moving average of span values for CO 92 as sensed by the analyzer 14 and a one minute moving average of span values for O 94 as sensed by the analyzer 14 are calculated by the averaging function block unit 78 of the data control unit 16. The span value averages 92 and 94 are then sent to the memory unit 32 of the computer 12 along line 80. The analyzer 14 then returns to analyzing a sample gas 96 from a coal pulverizer 98 and sending the signals indicative of $CO_e$ and $O_2$ content, 30 and 32 respectively, to the $CO_e$ signal unit 26 and the $O_2$ signal unit 28, respectively.

Figure 3:
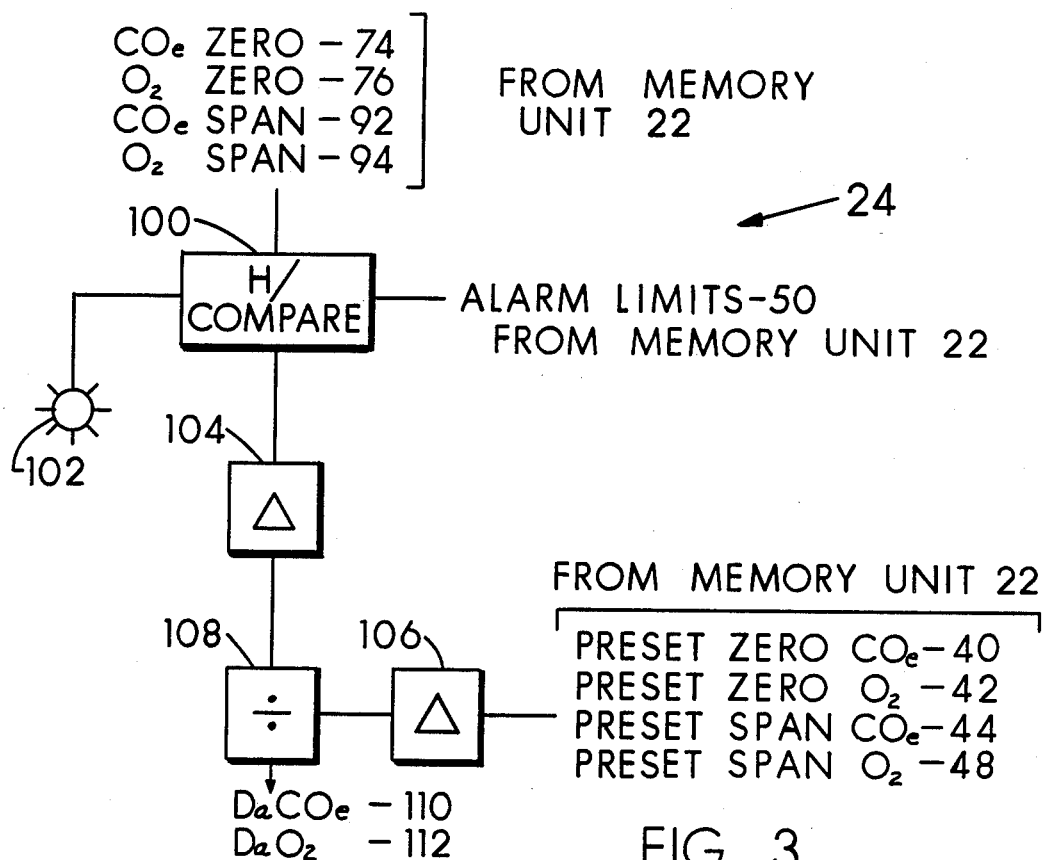
FIG. 3 is a logic diagram for the logic unit of FIG. 1.

Referring now to FIG. 3, when the data control unit 16 energizes the mechanical unit 18, it also energizes said memory unit 22. This allows the $CO_e$ and $O_2$ zero values, 74 and 76 respectively, and said $CO_e$ and $O_2$ span values, 92 and 94 respectively, to be stored in the memory unit 22.

When the memory unit 22 receives the zero values 74,76 and the span values 92,94 the logic unit 24 accesses them. Unit 24 first compares the values 74,76,92,94 to the preset alarm limits 50 in compare function block unit 100. If any of the zero or span values for $CO_e$ and $O_2$ 74,76,92,94 are above their respective alarm limits 50, an alarm 102 will alert the operator to an inferior calibration condition and he will take necessary steps to correct it, including but not limited to a manual adjustment on the analyzer. These instances are rare due to daily calibration and the daily cleaning operation 58.

The unit 24 then performs a calculation using the values 74,76,92,94; the preset optimum zero values for $CO_e$ and $O_2$, 40 and 42 respectively; and preset span values for $CO_e$ and $O_2$, 44 and 48 respectively. The preset values 40,42,44,48 are accessed from the memory unit 22. The calculations are performed in difference function block units 104 and 106 and a dividing function block unit 108. The same calculation is performed to both the $CO_e$ values 74,92,40,44 and the $O_2$ values 76,94,42,48 according to the following equation.

$$Da = \frac{P_s - P_z}{A_s - A_z}$$

Where:
Da=Drift Adjustment
$P_s$=Preset span value ($CO_e$—44 $O_2$—48)
$P_z$=Preset zero value ($CO_e$—40 $O_2$—42)
$A_s$=Actual span value ($CO_e$—92 $O_2$—94)
$A_z$=Actual zero value ($CO_3$—74 $O_2$—76)

The logic unit 24 sends calculated drift adjustments $DaCO_e$ 110 and $DaO_2$ 112 to the $CO_e$ signal unit 26 and the $O_2$ signal unit 28, respectively. The $DaCO_e$ 110 and $DaO_2$ 112 are the drift adjustments to be applied to the $CO_e$ and $O_2$ sample signals 30 and 32, respectively. The drift adjustments 110 and 112 minimize the drift of zero values 74,76 and span values 92,94 from their preset values 40,42 and 44,48, respectively.

Figure 4:
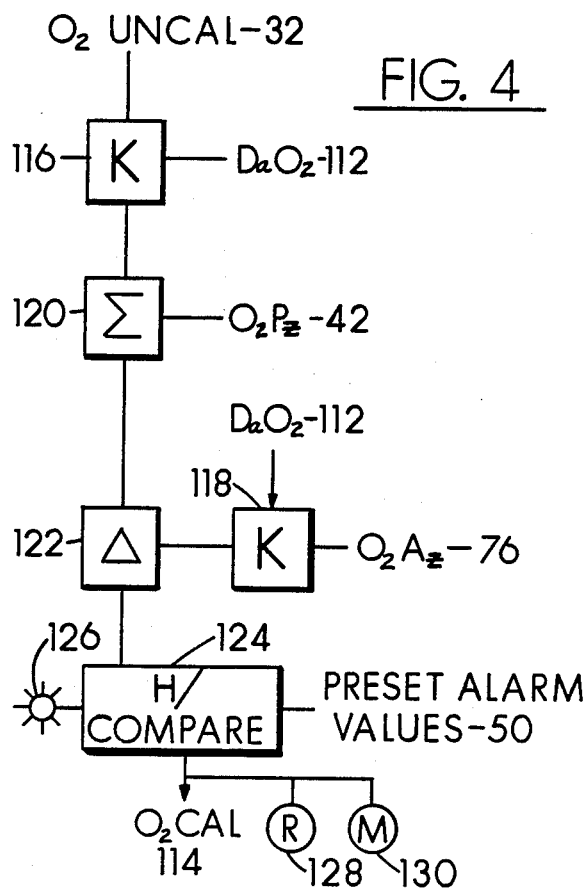
FIG. 4 is a logic diagram for the oxygen signal unit of FIG. 1.

The $O_2$ signal unit 28 embodied in FIG. 4 takes the $DaO_2$ calculation 112 from logic unit 24, and $O_2P_z$ value 42 and the $O_2A_z$ value 76 from memory unit 22, and $O_2$ uncalibrated sample signal 32 from analyzer 14 and performs the following calculation on them:

$$O_2Cal = Da(O_2s) + P_z - Da(A_z)$$

Where:
$O_2$ Cal=Calibrated $O_2$ output 114
Da=Drift adjustment 112
$O_2s$=$O_2$ sample signal 32
$P_z$=Preset $O_2$ zero value 42
$A_z$=Actual $O_2$ zero value 76

The calculation to arrive at said calibrated $O_2$ output 114 is achieved through proportional function block units 116 and 118, summation function block unit 120, and a difference function block unit 122.

The output 114 is continuously monitored in compare function block unit 124 to ensure that the coal pulverizer 98 being monitored does not turn into a potentially dangerous situation. When the output 114 goes above its preset alarm value 50, the operator is alerted of the dangerous situation by an alarm 126 and can take necessary steps to stabilize the coal pulverizer 98.

The output 114 is sent to a known chart recorder 128 and also may be displayed on a known CRT monitor 130.

The $O_2$ signal unit 28 creates a calibration line graph 132 through its calculation. It is depicted in FIG. 5. The $DaO_2$ value 112 is actually a proportion of error between the preset optimum scale and the scale the analyzer 14 is outputting. The $DaO_2$ value 112 is then multiplied by the analyzer $O_2$ output 32 to arrive at the calibrated $O_2$ output 114 with an offset added in for the preset zero value 42. The calibration graph 132 depicts the calibrated output 114, equal to 17.625% $O_2$ content, for the given uncalibrated analyzer output 32, equal to 19% $O_2$. This calculation is performed continuously on the uncalibrated output 32 to give the continuous calibrated $O_2$ signal 114.

Figure 6:
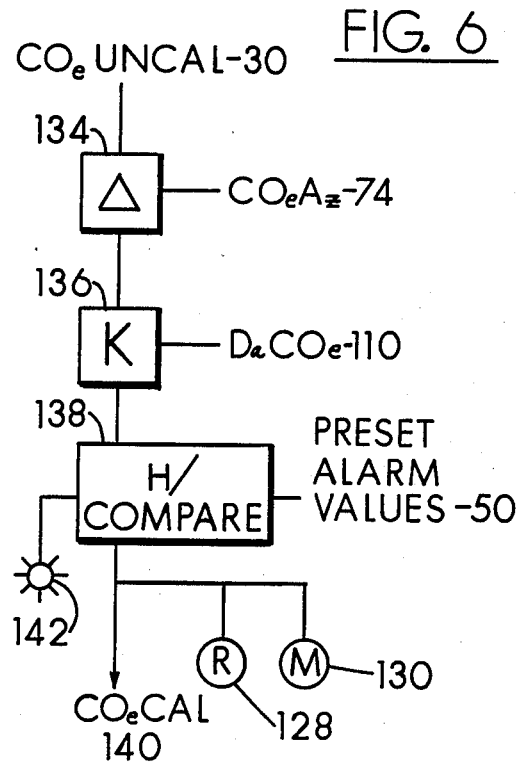
FIG. 6 is a logic diagram for the combustibles ($CO_e$) signal unit of FIG. 1.

The $CO_e$ signal unit 26 embodied in FIG. 6 operates in the same fashion as the $O_2$ signal unit 28. The $CO_e$ signal unit 26 uses the same calculation used in the $O_2$ signal unit 28 but performs this calculation using the $CO_e$ values 30,74,110. This calculation has no zero offset added in, however, because the said preset zero value 28 is always zero. This calculation is performed in a difference function block unit 134 and a proportional function block unit 136. The $CO_e$ signal unit also uses a compare function block unit 138 to monitor a calibrated $CO_e$ signal 140 and alert the operator to a dangerous condition through an alarm 142. The calibrated $CO_e$ signal 140 may also be displayed on the CRT 130 or the recorder 128.

A $CO_e$ calibration graph 144 is shown in FIG. 7.

It will be understood that certain modifications and improvements will occur to those skilled in the art upon a reading of this specification. All such modifications and improvements have been deleted herein for the sake of conciseness and readability but are properly intended to fall within the scope of the following claims.

What is claimed is:

1. An automatic, periodically calibrating system for continuous output of calibrated signals from a combined oxygen and combustibles analyzer comprising:
   a combined oxygen and combustibles analyzer for sensing a level of oxygen and a level of combustibles in a volatile atmosphere and for producing a first sample signal indicative of the oxygen level and a second sample signal indicative of the combustibles level;
   means for introducing zero and span calibration test gases into the analyzer;
   means for periodically calibrating the analyzer including:
   (a) a data control unit for automatically controlling the calibration of the analyzer, for presetting optimum zero and span values for oxygen and combustibles, and for presetting alarm limits for oxygen and combustibles;
   (b) a timer unit connected to the data control unit for setting discrete time intervals to activate the means for introducing the zero and span calibration test gases into the analyzer;
   (c) a mechanical unit, connected to the timer unit and to the analyzer, for introducing zero and span calibration test gases into said analyzer;
   (d) means for calculating zero and span values for oxygen and combustibles while the calibration test gases are introduced into the analyzer;
   (e) means for comparing said calculated zero and span values for oxygen and combustibles to the preset alarm limits for oxygen and combustibles;
   (f) means for activating an operator alarm if the zero and span values exceed the preset alarm limits for oxygen and combustibles;
   (g) means for calculating oxygen and combustibles drift adjustments based upon the zero and span values for oxygen and combustibles obtained form the calibration test gases, and upon the preset zero and span values for oxygen and combustibles;
   (h) a memory unit, connected to the data control unit, and to the means set forth in (d), (e), (f) and (g) above, for storing the preset optimum zero and span values, and the alarm limits; and
   means for applying the oxygen and combustibles drift adjustments concurrently to the first and second sample signals, according to a predetermined mathematical relationship, to obtain calibrated output signals indicative of the oxygen and combustibles levels in the volatile atmosphere.

2. A system according to claim 1, wherein the means for calculating zero and span values for oxygen and combustibles while the calibration test gases are introduced into the analyzer comprises: an oxygen signal unit for calculating a calibrated output signal indicative of the oxygen level in the calibration test gases and outputting the same, a combustibles signal unit for calculating a calibrated output signal indicative of the combustibles level in the calibration test gases and outputting the same, and a logic unit connected to said oxygen signal unit and to said combustibles signal unit.

3. A system according to claim 2 wherein the oxygen signal unit and the combustibles signal unit each further comprise a comparing unit for comparing the calibrated output signals indicative of the oxygen and combustibles levels to the preset alarm limits for oxygen and combustibles, respectively, and alarming means for alerting an operator whenever either of the comparing units indicates that the calibrated output signals indicative of the oxygen and combustibles levels are above the preset limits.

4. A system according to claim 1, wherein the data control unit has manual input means for inputting the optimum preset zero and span values of oxygen and combustibles and a manual override capability to allow an operator to commence a calibration sequence.

5. A system according to claim 1 wherein the means for calculating the oxygen and combustible signals drift adjustments applies the following mathematical relationships:

$$DaCO_e = \frac{P_sCO_e - P_zCO_e}{A_sCO_e - A_zCO_e} \ ; \ D_aO_2 = \frac{P_sO_2 - P_zO_2}{A_sO_2 - A_zO_2}$$

where:
$D_aCO_e$ = Drift Adjustment for Combustibles ($CO_e$)
$D_aO_2$ = Drift Adjustment for Oxygen ($O_2$)
$P_sCO_e$ = Preset Span Valve (for $CO_e$)
$P_sO_2$ = Preset Span Valve (for $O_2$)
$P_zCO_e$ = Preset Zero Valve (for $CO_e$)
$P_zO_2$ = Preset Zero Valve (for $O_2$)
$A_sCO_e$ = Actual Span Valve (for $CO_e$)
$A_sO_2$ = Actual Span Valve (for $O_2$)
$A_zCO_e$ = Actual Zero Valve (for $CO_e$)
$A_zO_2$ = Actual Zero Valve (for $O_2$).

6. A system according to claim 5 wherein the oxygen and combustibles drift adjustments are applied to the first and second sample signals according to the following mathematical relationships:

$$O_2 \text{ Cal} = D_aO_2 \times (O_2s) + P_zO_2 - D_aO_2 \times (A_zO_2)$$

$$CO_e \text{ Cal} = D_aCO_e(CO_es) - D_aCO_e \times (A_zCO_e)$$

where:
$O_2$ Cal = calibrated $O_2$ output
$CO_e$ Cal = calibrated $CO_e$ output
$D_aCO_e$ = Drift adjustment to $CO_e$
$D_aO_2$ = Drift adjustment to $O_2$
$CO_es$ = $CO_e$ sample signal
$O_2s$ = $O_2$ sample signal
$P_zO_2$ = Preset $O_2$ zero valve
$A_zCO_e$ = Actual $CO_e$ zero valve
$A_zO_2$ = Actual $O_2$ zero valve.

7. A system according to claim 1 wherein the means for periodically calibrating the analyzer further comprises a puffback cleaning unit for performing a cleaning operation in the analyzer for a duration long enough to purge said analyzer before introducing the zero and span calibration test gases into the analyzer.

8. A method of automatically and periodically calibrating output signals from a combined combustibles and oxygen analyzer comprising the steps of:
providing a source of predetermined time sequenced control signals;
purging the analyzer by backflushing atmospheric air through the analyzer for a predetermined period in response to the control signals;
establishing a signal indicative of the end of the purge;
introducing a zero calibration test gas to the analyzer in response to the signal indicative of the end of the purge and providing a signal indicative of the end of the zero calibration test gas introduction;
introducing a maximum scale value calibration test gas to the analyzer in response to the signal indicative of the end of the zero calibration test gas introduction and providing a signal indicative of the end of the maximum scale value calibration test gas introduction; and
adjusting an output of the analyzer to read zero and maximum scale upon the signal indicative of the end of the span gas introduction.

9. A method of claim 8 wherein the zero calibration test gas is concurrently made up of a gas content of 0 ppm combustibles and 1.0% oxygen.

10. A method of claim 8 wherein the maximum scale value calibration test gas is concurrently made up of a gas content of 250 ppm combustibles and 20.9% oxygen.

11. A method of claim 8 wherein a first sample signal indicative of a level of oxygen in a volatile atmosphere and a second sample signal indicative of a level of combustibles in a volatile atmosphere are adjusted concurrently.

* * * * *